US011622798B2

(12) United States Patent
Deirmengian et al.

(10) Patent No.: US 11,622,798 B2
(45) Date of Patent: *Apr. 11, 2023

(54) DEVICE AND METHOD FOR NORMALIZING IMPLANT STRAIN READINGS TO ASSESS BONE HEALING

(71) Applicant: DEPUY SYNTHES PRODUCTS, INC., Raynham, MA (US)

(72) Inventors: Carl Deirmengian, West Chester, PA (US); George Mikhail, West Chester, PA (US); Glen Pierson, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 478 days.

This patent is subject to a terminal disclaimer.

(21) Appl. No.: 16/862,247

(22) Filed: Apr. 29, 2020

(65) Prior Publication Data

US 2020/0253651 A1 Aug. 13, 2020

Related U.S. Application Data

(63) Continuation of application No. 15/709,137, filed on Sep. 19, 2017, now Pat. No. 10,675,069, which is a continuation of application No. 13/355,970, filed on Jan. 23, 2012, now Pat. No. 9,795,423.

(51) Int. Cl.
| *A61B 17/80* | (2006.01) |
| *A61B 5/103* | (2006.01) |
| *A61B 5/07* | (2006.01) |
| *A61B 5/00* | (2006.01) |

(Continued)

(52) U.S. Cl.
CPC .............. *A61B 17/80* (2013.01); *A61B 5/076* (2013.01); *A61B 5/103* (2013.01); *A61B 5/4504* (2013.01); *A61B 2017/00221* (2013.01); *A61B 2090/064* (2016.02); *A61B 2562/0261* (2013.01)

(58) Field of Classification Search
CPC ......... A61B 5/076; A61B 17/80; A61B 5/103; A61B 5/4504; A61B 2090/064; A61B 2017/00221; A61B 2562/0261
See application file for complete search history.

(56) References Cited

U.S. PATENT DOCUMENTS

| 6,001,099 A | 12/1999 | Huebner |
| 6,034,296 A * | 3/2000 | Elvin .................. A61B 5/0031 128/903 |
| 8,926,674 B2 | 1/2015 | Wolter et al. |

(Continued)

FOREIGN PATENT DOCUMENTS

| CN | 102123657 | 7/2011 |
| DE | 10-2006-006341 | 8/2007 |

(Continued)

*Primary Examiner* — Daniel L Cerioni
(74) *Attorney, Agent, or Firm* — Fay Kaplun & Marcin, LLP

(57) ABSTRACT

A device and method for treating a bone includes a bone plate including first and second portions joined to one another via a connecting portion, a rigidity of the connecting portion being less than rigidities of each of the first and second portions in combination with a first sensor mounted on the first portion measuring strain on the first portion and a second sensor mounted on the second portion measuring strain on the second portion.

17 Claims, 5 Drawing Sheets

(51) Int. Cl.
 *A61B 90/00* (2016.01)
 *A61B 17/00* (2006.01)

(56) References Cited

U.S. PATENT DOCUMENTS

| | | |
|---|---|---|
| 2002/0049394 A1 | 4/2002 | Roy et al. |
| 2006/0052782 A1 | 3/2006 | Morgan et al. |
| 2007/0134623 A1 | 6/2007 | Essiger |
| 2008/0161729 A1 | 7/2008 | Bush |
| 2008/0300597 A1 | 12/2008 | Morgan et al. |
| 2010/0217156 A1 | 8/2010 | Fisher et al. |
| 2011/0098603 A1 | 4/2011 | Deirmengian et al. |
| 2012/0253345 A1 | 10/2012 | Wixted |

FOREIGN PATENT DOCUMENTS

| | | |
|---|---|---|
| DE | 10-2006-034041 | 1/2008 |
| DE | 10-2010-022434 | 12/2011 |
| DE | 10-2011-115283 | 4/2013 |
| JP | 2006-506194 | 2/2006 |
| RU | 2396900 | 8/2010 |
| WO | 2004/045455 | 6/2004 |
| WO | 2007/090543 | 8/2007 |
| WO | 2009/146089 | 12/2009 |
| WO | 2011/050149 | 4/2011 |

\* cited by examiner

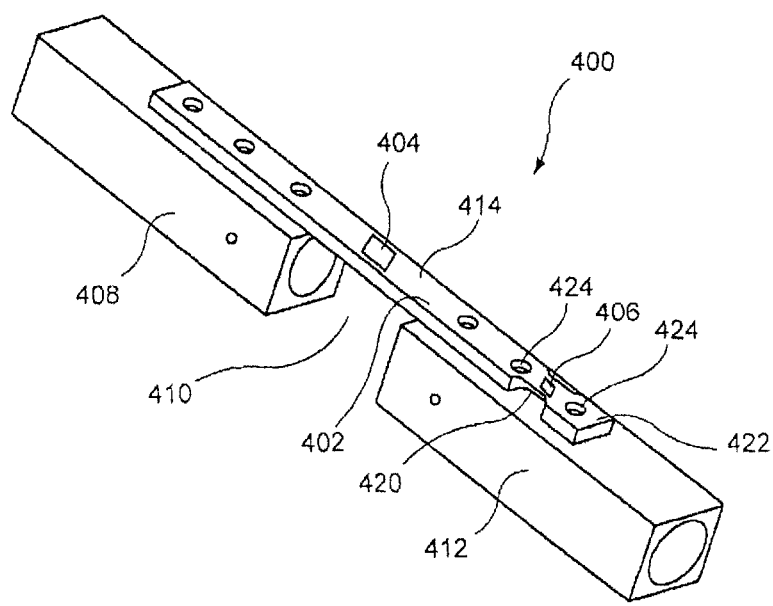
F I G. 5

US 11,622,798 B2

DEVICE AND METHOD FOR NORMALIZING IMPLANT STRAIN READINGS TO ASSESS BONE HEALING

BACKGROUND

Strain gages can be placed on orthopedic implants to track the progress of bone healing. Upon initial implantation, the implants are expected to experience higher levels of strain which decrease during healing as the bone begins to share more of the load with the implant. Currently, however, implant strain values need to be assessed with a known load applied to the bone in order to evaluate bone healing.

SUMMARY OF THE INVENTION

The present invention relates to a device and method for treating a bone includes a bone plate including first and second portions joined to one another via a connecting portion, a rigidity of the connecting portion being less than rigidities of each of the first and second portions along with a first sensor mounted on the first portion measuring strain on the first portion and a second sensor mounted on the second portion measuring strain on the second portion.

BRIEF DESCRIPTION OF THE DRAWINGS

FIG. 5 shows a perspective view of a system according to a fourth exemplary embodiment of the present invention;

DETAILED DESCRIPTION

Figure 1:
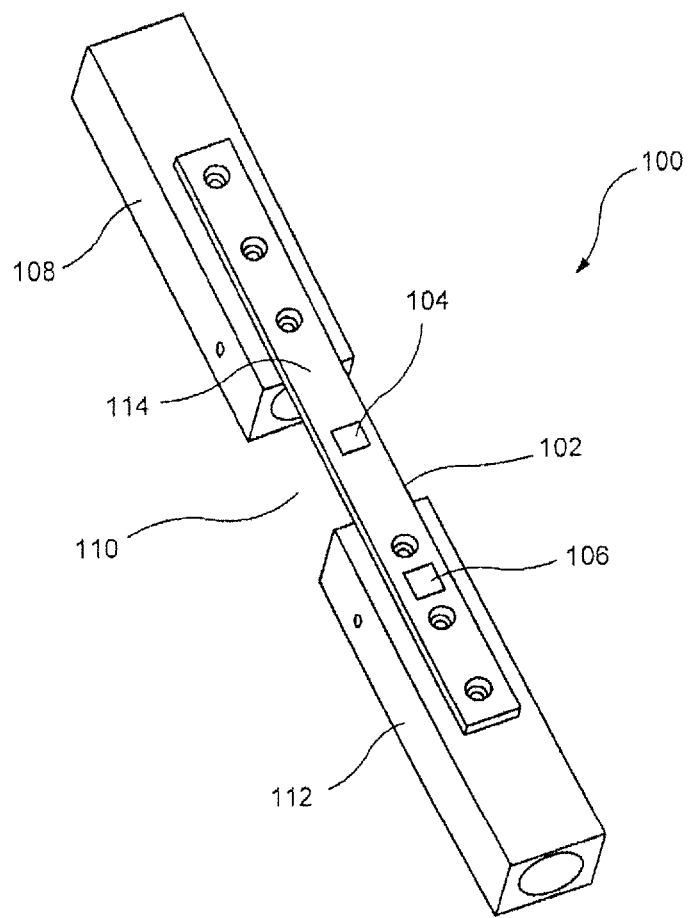
FIG. 1 shows a perspective view of a system according to a first exemplary embodiment of the present invention.

The present invention may be further understood with reference to the following description and the appended drawings, wherein like elements are referred to with the same reference numerals. The exemplary embodiment of the present invention relate to a system and method for tracking the progress of bone healing. In particular, the exemplary embodiments describe systems and methods that calculate a ratio of strain at multiple locations along an implant and/or a bone. An exemplary embodiment of the system may include a first sensor on a surface of the implant adapted to be positioned at a location proximate a weakened portion of the bone. Strain on the implant at this location will be affected by the strength or stiffness of the weakened bone and the load placed on the bone by the patient. A second sensor may be placed on the implant at a location in which strain measured by the second sensor is affected only by the load placed on the bone such that the measured strain is substantially unchanged by the bone healing process. Thus, a ratio between the strains measured by the first and second sensors provides information corresponding to bone healing, regardless of the load on the bone. It will be understood by those of skill in the art that although the exemplary embodiment specifically describe tracking the healing progress of a leg bone, the present invention may be used to track the progress of healing of any load bearing bone. It will also be understood by those of skill in the art that although the exemplary embodiments specifically show and describe two sensors, the present invention may include additional sensors along different areas of the bone to determine ratios corresponding to the bone healing progress of the different areas. In addition, although exemplary embodiments show a bone plate, the present invention may be used with any other fixation element such as, for example, screws, intramedullary devices, external fixators, spine fixation implants and prosthetics.

As shown in FIG. 1, a system 100 according to a first exemplary embodiment of the invention comprises an implant 102 (e.g., a bone plate) and first and second sensors 104, 106, respectively. The implant 102 is configured for fixation over a target portion of a bone 108 to, for example, fix a fracture 110 or to support a weakened portion of the bone 108. The first and second sensors 104, 106 are mounted along a surface 114 of the implant 102 such that the first and second sensors 104, 106 may be mechanically coupled to the bone 108. Although the surface 114 is shown as facing away from the bone 108 when the implant 102 is fixed to the bone 108 in a desired location, it will be understood by those of skill in the art that the sensors 104, 106 may be mounted along any surface of the implant 102. For example, the sensors 104, 106 may also be mounted on a surface of the implant 102 facing the bone 108 or a surface on a side of the implant 102. The first and second sensors 104, 106, respectively, are positioned on the implant 102 so that, when the implant is in a desired position on the bone 108, the first sensor 104 is located over a site of the fracture 110 while the second sensor 106 is separated from the fracture 110 over a healthy (i.e., solid) portion 112 of the bone 108 to measure levels of strain and/or load on the implant 102, at these positions along the implant 102. The second sensor 106 should be isolated between two screws locked in a healthy portion 112 of the bone 108 to measure a load on the bone 108.

The sensors 104, 106 in this embodiment may be passively powered MEMs sensors that are used to measure strain and include an interface for wireless connection to a data collection device as would be understood by those skilled in the art. In another embodiment, the sensors 104, 106 may be powered chips that are connected to a printed circuit board (PCB). This permits strain on the implant 102 to be measured and transmitted to the data collection device for further processing without physically accessing the sensors 104, 106. It will be understood by those of skill in the art that the strain measurements detected by the sensors 104, 106 are not required to represent actual strain values, but may include any signal that changes based on changing strains of their substrates. For example, the MEMS sensors 104, 106 may be RF devices that deform when a strain is placed thereon, resulting in a frequency shift caused by a change in capacitance of the sensors 104, 106 such that the frequency shift corresponds to a change in strain. As would be understood by those skilled in the art, an external device may be employed to wirelessly provide a signal to the sensors 104, 106. Changes in a returned signal may then be measured to determine a level of strain to which the sensor is subject. A ratio of the strain measured by the first sensor 104 to the strain measured by the second sensor 106 may then be determined by a physician or other professional to track healing progress. Alternatively, the ratio may be determined by a processing device that may also store the strain measurements and the determined ratios (e.g., in an internal memory or on an external storage device) so that changes in the ratio may be reviewed to more fully understand the progression of the healing over time.

It will be understood by those of skill in the art that when the bone 108 is initially broken or fractured, strain on the implant 102 at the location of the fracture 110 will vary based on changing mechanical properties of the bone 108 during the healing process and the load placed on the bone 108 (e.g., the weight that the patient places on the leg) while the strain measured in the healthy portion 112 varies based only on the load placed on the bone 108. Thus, taking a ratio of the strains measured by the two sensors 104, 106 normalizes the effects of the load on the sensors 104, 106 providing data corresponding to the stiffness of the bone 108 at the fracture site 110. The ratio of the measurements from the first sensor 104 to the measurements from the second sensor 106 during the healing process should trend in a decreasing pattern over time, whereas a lack of healing would show no recognizable trend over time.

Figure 2:
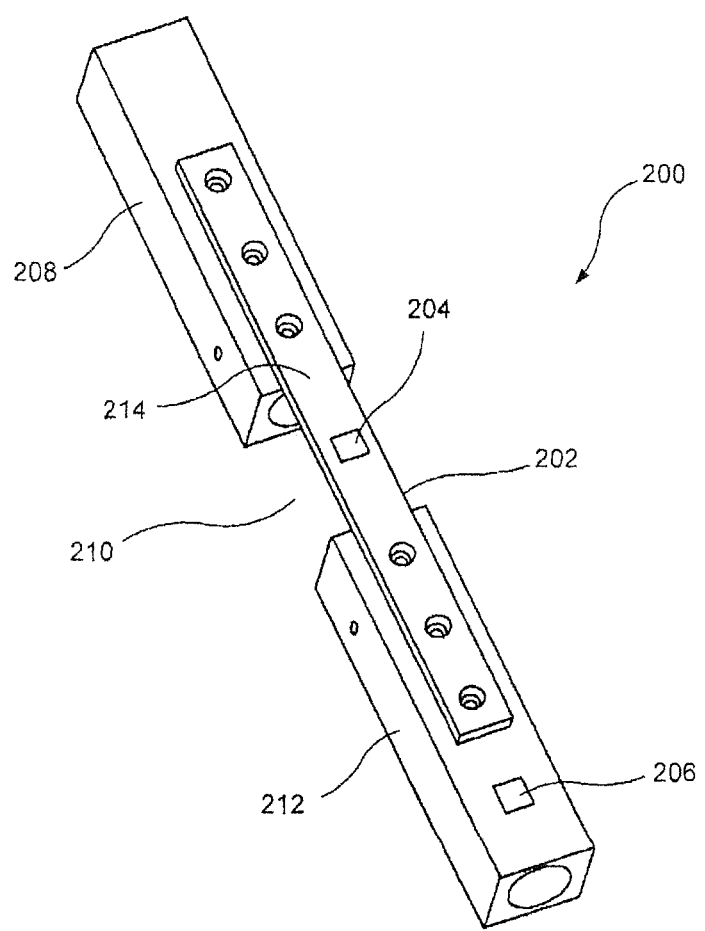
FIG. 2 shows a perspective view of a system according to a second exemplary embodiment of the present invention.

As shown in FIG. 2, a system 200 according to a second exemplary embodiment of the invention is substantially similar to the system 100, including an implant 202 and at least two sensors 204, 206. However, rather than both sensors 204, 206 being positioned on the implant 202, the first sensor 204 is located on a surface 214 of the implant 202 in a position corresponding to a fracture of a bone 208, while the second sensor 206 is placed directly on a solid portion 212 of the bone 208, outside a perimeter of the implant 202. Thus, the first sensor 204 measures strain on the implant 202 at a position corresponding to the site of the fracture 210 while the second sensor 206 measures strain on the solid portion 212 of the bone 208. Similarly to the system 100, a ratio between the strains measured by the first and second sensors 204, 206 is determined and tracked to study the progress of healing in the bone 208. As indicated above, the ratio of the strain measurements from the first sensor 204 to the strain measurements from the second sensor 206 trend in a decreasing pattern as the bone 208 heals, whereas a lack of healing will show no recognizable trend over time.

Figure 4:
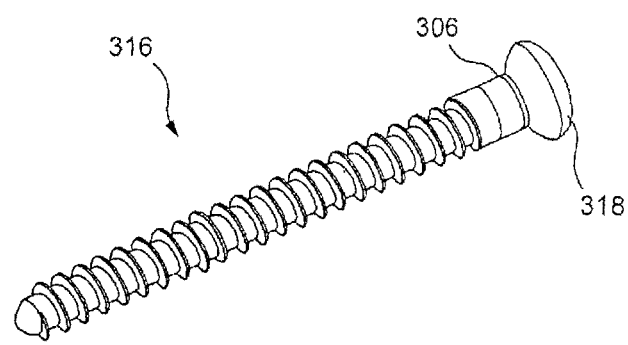
FIG. 4 shows a side view of a bone fixation element of the system of FIG. 3.
Figure 3:
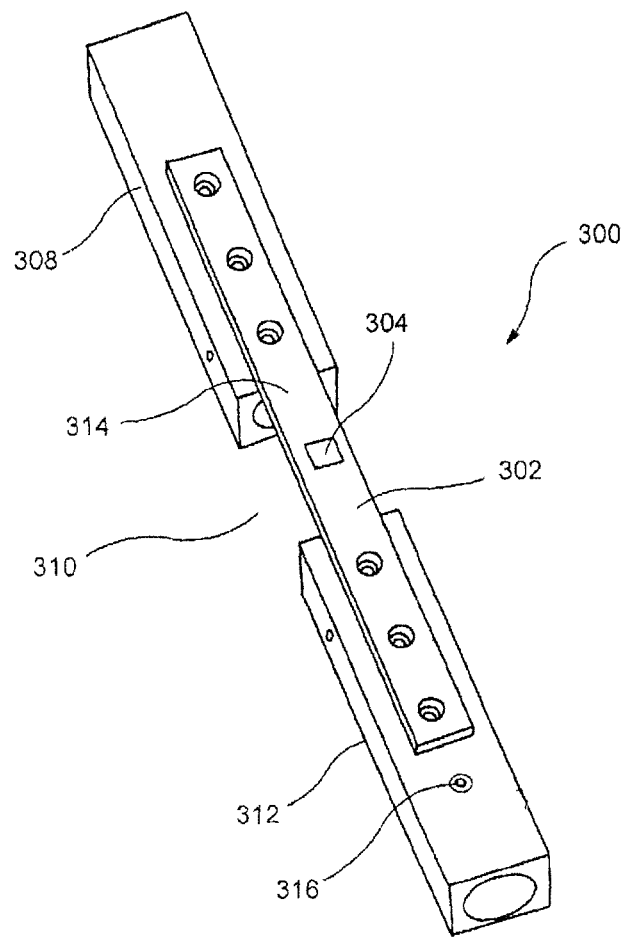
FIG. 3 shows a perspective view of a system according to a third exemplary embodiment of the present invention.

As shown in FIGS. 3-4, a system 300 according to a third exemplary embodiment of the invention is substantially similar to the system 200, comprising an implant 302 and at least two sensors 304, 306. Similarly to the first sensor 204, the first sensor 304 is placed on a surface 314 of the implant 302 in a location corresponding to a position of a fracture 310 of a bone 308 (when the implant 302 is mounted on the bone 308 in a desired position) to measure strain on the implant 302 at the position of the fracture 310 while the second sensor 306 is placed directly on a solid portion 312 of the bone 308. However, rather than being placed on an exterior surface of the bone 308, the second sensor 306 is placed within the solid portion 312 via, for example, a bone fixation element 316 (e.g., screw).

The second sensor 306 may be attached adjacent to a proximal end 318 of the bone fixation element 316 such that when the bone fixation element 316 is inserted into the solid portion 312 of the bone, the second sensor 306 contacts a cortical wall of the bone 308. The second sensor 306 may be printed or mounted around a portion of the bone fixation element 316 to measure deformation of the bone 308 which is directly related to strain on the bone 308. The ratio of the measurements from the first sensor 304 to those of the second sensor 306 may then be determined to track healing progress in the same manner described above.

As shown in FIG. 5, a system 400 according to a fourth exemplary embodiment of the invention is substantially similar to the system 100, comprising an implant 402 and first and second sensors 404, 406, respectively, both of which are mounted on the implant 402. Similarly to the first sensor 104, the first sensor 404 is located on the implant 402 in a position which, when the implant 402 is in the desired position, corresponds to the location of a fracture 410 so that the first sensor 404 measures strain on the implant 402 at a position corresponding to the site of the fracture 410. The second sensor 406 is positioned on a portion 420 of the implant 402 having greater flexibility than the portion of the implant 402 on which the first sensor 404 is mounted. For example, the portion 420 may be made more flexible than other portions of the implant 402 by reducing a width (i.e., an extent of the implant 402 across a bone facing surface thereof in a direction perpendicular to a longitudinal axis of the implant 402) and/or a thickness of the portion 420 (i.e., a distance between the bone facing surface and a surface thereof which faces away from the bone) as compared to remaining portions of the implant 402. In a preferred embodiment, the flexible portion 420 is adjacent to an end 422 of the implant 402 so that the second sensor 406 is separated from the fracture 410 by a distance great enough to ensure that the underlying portion 412 of the bone 408 is solid.

The second sensor 406 on the flexible portion 420 of the implant 402 is fixed to the solid portion 412 of the bone 408 via, for example, locking screws inserted in holes 424 on opposing sides thereof. The second sensor 406 measures strain on a portion of the implant 402 corresponding to the solid portion 412 of the bone 408 so that measurements from the second sensor 406 may be used to normalize measurements from the first sensor. Similarly to the placement of a sensor directly in or on a bone, as described in conjunction with systems 200 and 300, placing the second sensor 406 on a more flexible portion 420 of the implant 402 between two locked screws permits a more accurate measurement of the strain on the underlying solid portion 412 of the bone 408, as compared to the results from placing the second sensor 406 on a stiffer portion of the implant 402. The ratio of the measurements from the first sensor 404 to the measurements from the second sensor 406 during the healing process should trend in a pattern indicating an increasing stiffness of the bone 408 over time, whereas a lack of healing should show no recognizable trend over time.

Figure 6:
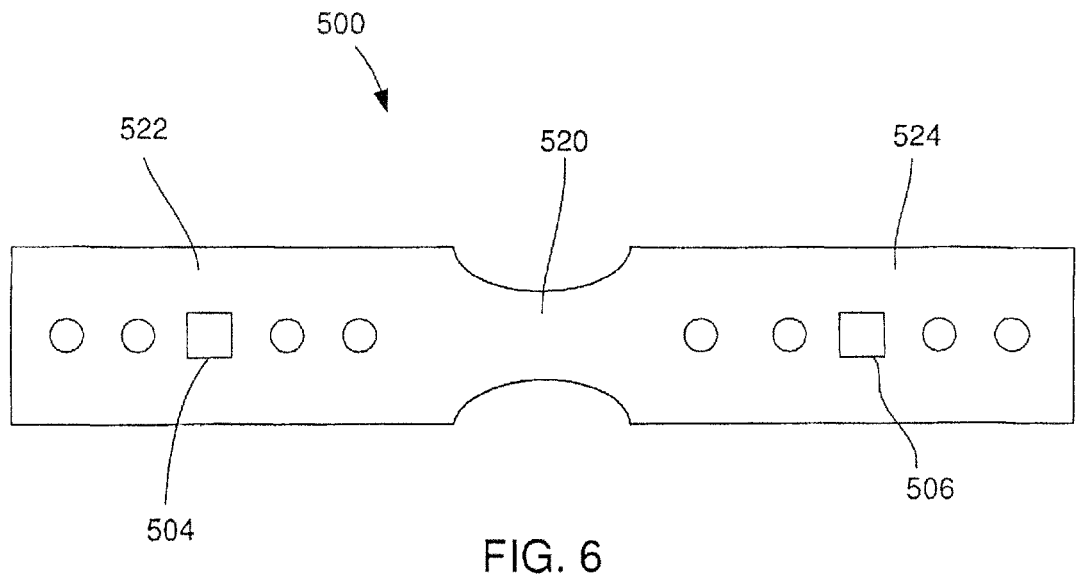
FIG. 6 shows a top plan view of a system according to a fifth exemplary embodiment of the present invention.

As shown in FIG. 6, a system 500 according to another exemplary embodiment of the present invention may be substantially similar to the system 100, comprising a bone plate 502 and first and second sensors 504, 506, respectively. The first and second sensors 504, 506 are mounted along a surface 514 of the bone plate 502 such that the first and second sensors 504, 506 may be mechanically coupled to a bone via the bone plate 502. The first and second sensors 504, 506 are positioned on the bone plate 502 so that when the bone plate 502 is in a desired position along the bone, the first sensor 504 is located over a site of a fracture of the bone while the second sensor 506 is separated from the fracture (preferably over a healthy (e.g., solid) portion of bone) as described above in regard to the system 100. The first and second sensors 504, 506 measure a level of strain on the bone plate 502 at these positions of the bone plate 502 and a ratio of the strains measured by the first and second sensors 504, 506 indicates a progression of healing of the bone over time.

In contrast to the system 100, the bone plate 502 includes a first portion 522 and a second portion 524 connected to one another via a connecting portion 520 with the first sensor 504 mounted to the first portion 522 and the second sensor 506 is mounted to the second portion 524 on a side of the connecting portion 520 opposite the first portion 522. Thus, when the first portion 522 is positioned such that the first sensor 504 overlies a fracture site while the second portion 524 is positioned such that the second sensor 506 extends over a healthy portion of bone, the connecting portion 520 extends between the first and second sensors 504, 506. The connecting portion 520 is designed to reduce strain transmitted between the first and second portions 522, 524. Specifically, the connecting portion 520 is less rigid than the first and second portions to reduce a torsion strain applied to the second sensor 524. For example, a width of the connecting portion 520 may be reduced relative to the widths of the first and second portions 522, 524 to render the connecting portion 520 more flexible than the first and second portions 522, 524. This reduces the rigidity of the bone plate 502 across the surface 514 in a direction substantially perpendicular to a longitudinal axis of the bone plate 502, more substantially mechanically separating the second sensor 506 from strains associated with the fracture site (i.e., reducing torsion strains applied across the fracture site and transmitted to the second sensor 506) so that the second sensor 506 more accurately measures levels of strain associated only with the healthy portion of bone. It will be understood by those of skill in the art that the first sensor 504, which is located over the fracture site, detects bending strain which are significantly greater than any torsion strains detected thereby so that these torsion strains have an insubstantial impact on the total strain measured by the first sensor 504.

Figure 7:
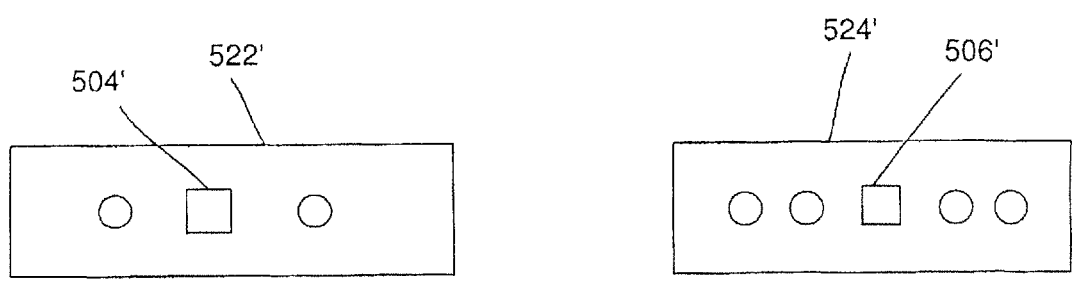
FIG. 7 shows a top plan view of a system according to an alternate embodiment of the present invention.

In an another example, the connecting portion 520 may be formed as a frangible link designed to fail when a torsion force applied thereto exceeds a predetermined threshold level. Thus, before the frangible link is broken, the second sensor 506 is subject to torsion strains limited by the threshold level and, after the frangible link has been severed, the first and second portions 522, 524 of the bone plate 502 are completely separated and isolated from one another eliminating the impact on the second sensor 506 of any torsion strains arising over the fracture site. Those skilled in the art will understand that the threshold level at which the connecting portion 520 fails is preferably set so that, when the frangible link is not broken, the maximum level of torsion strain transmitted from the first portion 522 to the second sensor 506 are insignificant as compared to the strain levels expected to be seen in the healthy bone. In another alternate embodiment, as shown in FIG. 7, a system 500' comprises two separate bone plates 522', 524' on which first and second sensors 504', 506' are mounted, respectively. The first and second bone plates 522', 524' are not connected to one another allowing the first plate 522' to be attached over a fracture site while the second plate 524' is separated therefrom and attached over a healthy portion of bone to completely eliminate the transmission of torsion from the fracture site to the second sensor 506'.

It will be understood by those of skill in the art that other mechanisms may be employed for normalizing measurements of strain on a portion of an implant which, when mounted on a bone in a target location, corresponds to a position of a fracture or other weakened portion of that bone. For example, the patient may be provided with load sensors on which to push or stand with the affected limb such that a load measurement may be taken simultaneously with a strain measurement of the sensor on the implant. Alternatively, the patient may be provided with a sensor (e.g., placed in the sole of a shoe) to measure the load placed on the affected leg, if the affected bone is the femur or tibia.

It will be apparent to those skilled in the art that various modifications and variations can be made in the structure and the methodology of the present invention, without departing from the spirit or the scope of the invention. Thus, it is intended that the present invention cover the modifications and variations of this invention provided that they come within the scope of the appended claims and their equivalents.

What is claimed is:

1. A method, comprising:
   coupling a first portion of a bone fixation device to a bone with a first sensor of the bone fixation device positioned adjacent to a fracture site;
   coupling a second portion of the bone fixation device to a heathy portion of the bone;
   measuring a strain on the first portion of the bone fixation device including the first sensor;
   measuring a strain on the second portion of the bone fixation device including a second sensor; and
   determining a ratio of the strain measured by the first sensor to the strain measured by the second sensor to normalize an effect of loads on the bone and determine a level of healing of the hone.

2. The method of claim 1, wherein the second sensor is coupled to the second portion of the bone fixation device, and further comprising coupling the second portion of the bone fixation device to the healthy portion of the bone via first and second bone screws positioned on opposite sides of the second sensor.

3. The method of claim 1, wherein the second sensor is directly coupled to the healthy portion of the bone.

4. The method of claim 2, wherein the first and second portions of the bone fixation device are connected to one another via a connecting portion of the bone fixation device which has a rigidity less than each of the first and second portions of the bone fixation device to reduce a level of strain transmitted between the first and second portions of the bone fixation device through the connection portion of the bone fixation device.

5. The method of claim 4, wherein the bone fixation device has a length along a longitudinal axis thereof and a width transverse thereto, the connecting portion having a width smaller than widths of the first and second portions of the bone fixation device.

6. The method of claim 4, wherein the hone fixation device is a bone plate.

7. The method of claim 4, wherein the hone fixation device is an intramedullary device.

8. The method of claim 4, wherein the connecting portion is formed as a frangible link designed to fail when a torsion to which the frangible link is subjected exceeds a predetermined level.

9. The method of claim 1, wherein each of the first and second sensors is one of a MEM sensor, a strain gauge and a powered chip connected to a printed circuit board.

10. The method of claim 1, wherein the first and second sensors are configured to permit data collected thereby to be read wirelessly via a device external to a body within which the first and second sensors have been implanted.

11. The method of claim 3, wherein the second sensor is included on a bone screw inserted into the healthy portion of the hone.

12. The method of claim 1, wherein the first sensor includes a passively powered chip.

13. The method of claim 1, wherein the first and second sensors wirelessly provide data to an external data gathering unit.

14. The method of claim 1, wherein the ratio of the strain measured by the first sensor to the strain measured by the second sensor is determined by a processing unit.

15. The method of claim 2, wherein the first portion of the bone fixation device is not connected to the second portion of the hone fixation device.

16. The method of claim 3, wherein the second sensor is positioned on an exterior surface of the healthy portion of the bone.

17. The method of claim 1, wherein the bone fixation device is a bone plate, further comprising coupling the bone plate to the bone via a plurality of screws inserted through a plurality of variable angle holes on an exterior surface of the bone plate, the variable angle holes running through the bone plate from the exterior surface of the bone plate to an interior surface of the bone plate, the interior surface contacting the bone.

* * * * *

UNITED STATES PATENT AND TRADEMARK OFFICE
CERTIFICATE OF CORRECTION

| | | |
|---|---|---|
| PATENT NO. | : 11,622,798 B2 | |
| APPLICATION NO. | : 16/862247 | |
| DATED | : April 11, 2023 | |
| INVENTOR(S) | : Deirmengian et al. | |

It is certified that error appears in the above-identified patent and that said Letters Patent is hereby corrected as shown below:

In the Claims

Claim 1, Column 6, Line 23:
"a level of healing if the hone." should read "a level of healing if the bone."

Claim 6, Column 6, Line 45:
"6. The method of claim 4, wherein the hone fixation" should read "6. The method of claim 4, wherein the bone fixation"

Claim 7, Column 6, Line 47:
"7. The method of claim 4, wherein the hone fixation" should read "7. The method of claim 4, wherein the bone fixation"

Claim 11, Column 6, Line 62:
"the hone." should read "the bone."

Claim 15, Column 7, Line 6:
"of the hone fixation device." should read "of the bone fixation device."

Signed and Sealed this
Twenty-third Day of May, 2023

Katherine Kelly Vidal
*Director of the United States Patent and Trademark Office*